(12) United States Patent
Shinoda

(10) Patent No.: US 9,833,166 B2
(45) Date of Patent: Dec. 5, 2017

(54) MAGNETIC RESONANCE IMAGING APPARATUS CONFIGURED TO ACQUIRE TARGET SITE DIAGNOSTIC IMAGE DATA BASED ON DETECTION OF TARGET SITES IN PRIOR ACQUIRED IMAGE DATA

(71) Applicant: Toshiba Medical Systems Corporation, Otawara-shi (JP)

(72) Inventor: Kensuke Shinoda, Tochigi (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 441 days.

(21) Appl. No.: 14/487,328

(22) Filed: Sep. 16, 2014

(65) Prior Publication Data

US 2015/0077114 A1 Mar. 19, 2015

(30) Foreign Application Priority Data

Sep. 18, 2013 (JP) ................................ 2013-193409

(51) Int. Cl.
| | | |
|---|---|---|
| A61B 5/055 | (2006.01) | |
| A61B 5/00 | (2006.01) | |
| G01R 33/56 | (2006.01) | |
| G01R 33/483 | (2006.01) | |
| G01R 33/48 | (2006.01) | |
| G01R 33/54 | (2006.01) | |

(52) U.S. Cl.
CPC ............ *A61B 5/055* (2013.01); *A61B 5/0037* (2013.01); *G01R 33/4833* (2013.01); *A61B 5/4566* (2013.01); *G01R 33/4822* (2013.01); *G01R 33/4835* (2013.01); *G01R 33/546* (2013.01); *G01R 33/5608* (2013.01)

(58) Field of Classification Search
CPC ............ G01R 33/4833; G01R 33/4822; G01R 33/4835; G01R 33/546; G01R 33/5608; A61B 5/055; A61B 5/0037; A61B 5/4566
See application file for complete search history.

(56) References Cited

U.S. PATENT DOCUMENTS

| | | | | |
|---|---|---|---|---|
| 2008/0071166 | A1* | 3/2008 | Miyazaki ........... | G01R 33/5635 600/419 |
| 2011/0206260 | A1* | 8/2011 | Bergmans ............ | G01R 33/543 382/131 |
| 2011/0228998 | A1* | 9/2011 | Vaidya ................. | G01R 33/543 382/131 |
| 2012/0226141 | A1* | 9/2012 | Shinoda ................. | G01R 33/48 600/419 |

FOREIGN PATENT DOCUMENTS

| | | |
|---|---|---|
| JP | 2005-237968 | 9/2005 |
| JP | 2012-045192 | 3/2012 |

* cited by examiner

*Primary Examiner* — G. M. Hyder
(74) *Attorney, Agent, or Firm* — Nixon & Vanderhye P.C.

(57) ABSTRACT

A magnetic resonance imaging apparatus according to an embodiment includes a specifying unit and an acquiring unit. The specifying unit specifies, on a basis of a detection result of target sites of a subject detected from an image on which the target sites are visualized, a first region and a second region which is different from the first region on the image. The acquiring unit acquires data of the second region by using an imaging condition which is different from an imaging condition on an imaging slice and used for acquiring data of the first region.

10 Claims, 9 Drawing Sheets

FIG.7
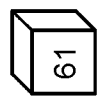
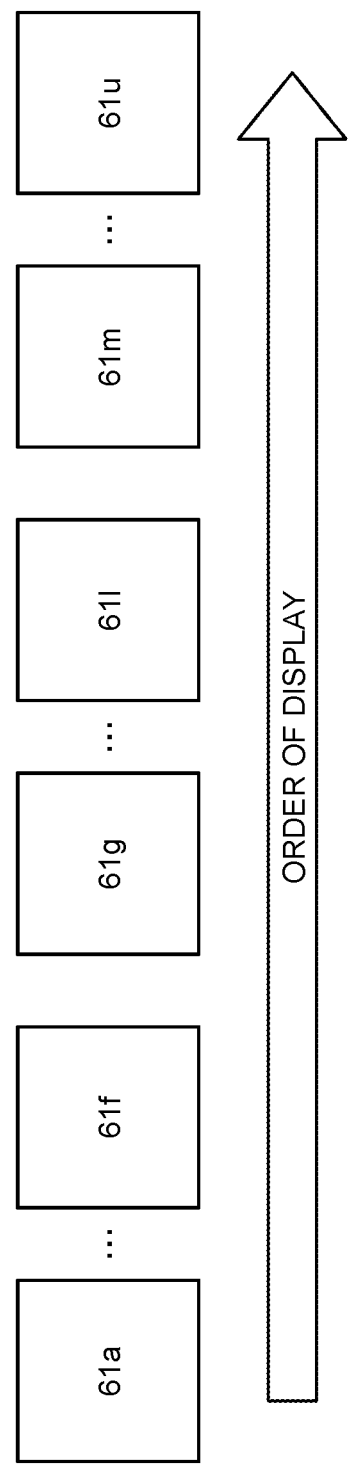

MAGNETIC RESONANCE IMAGING APPARATUS CONFIGURED TO ACQUIRE TARGET SITE DIAGNOSTIC IMAGE DATA BASED ON DETECTION OF TARGET SITES IN PRIOR ACQUIRED IMAGE DATA

CROSS-REFERENCE TO RELATED APPLICATIONS

This application is based upon and claims the benefit of priority from Japanese Patent Application No. 2013-193409, filed on Sep. 18, 2013; the entire contents of which are incorporated herein by reference.

FIELD

Embodiments described herein relate generally to a magnetic resonance imaging (MRI) apparatus.

BACKGROUND

Conventionally, to perform a medical examination on intervertebral discs by using an MRI apparatus, a slice image parallel to an intervertebral disc and including the intervertebral disc are taken. To perform such a medical examination, for example, a method is known by which an MRI apparatus automatically detects intervertebral discs from a detection-purpose image on which the spine of a subject is visualized and determines positions of imaging slices with respect to the detected intervertebral discs. Another method is also known by which vertebral bodies are similarly detected, so that positions of imaging slices are determined with respect to the detected vertebral bodies. When a medical examination is performed by using either of these methods, there are some situations where the detection of the intervertebral discs or the vertebral bodies fails in a region where the contrast of the intervertebral discs or the vertebral bodies is weak on the detection-purpose image.

BRIEF DESCRIPTION OF THE DRAWINGS

FIG. 7 is a drawing of an example of a display of slice images in the second mode implemented by the display controlling unit according to the present embodiment;

DETAILED DESCRIPTION

An MRI apparatus according to an embodiment includes a specifying unit and an acquiring unit. The specifying unit specifies, on a basis of a detection result of target sites of a subject detected from an image on which the target sites are visualized, a first region and a second region which is different from the first region on the image. The acquiring unit acquires data of the second region by using an imaging condition which is different from an imaging condition on an imaging slice and used for acquiring data of the first region.

The MRI apparatus according to the present embodiment will be explained in detail below, with reference to the drawings.

Figure 1:
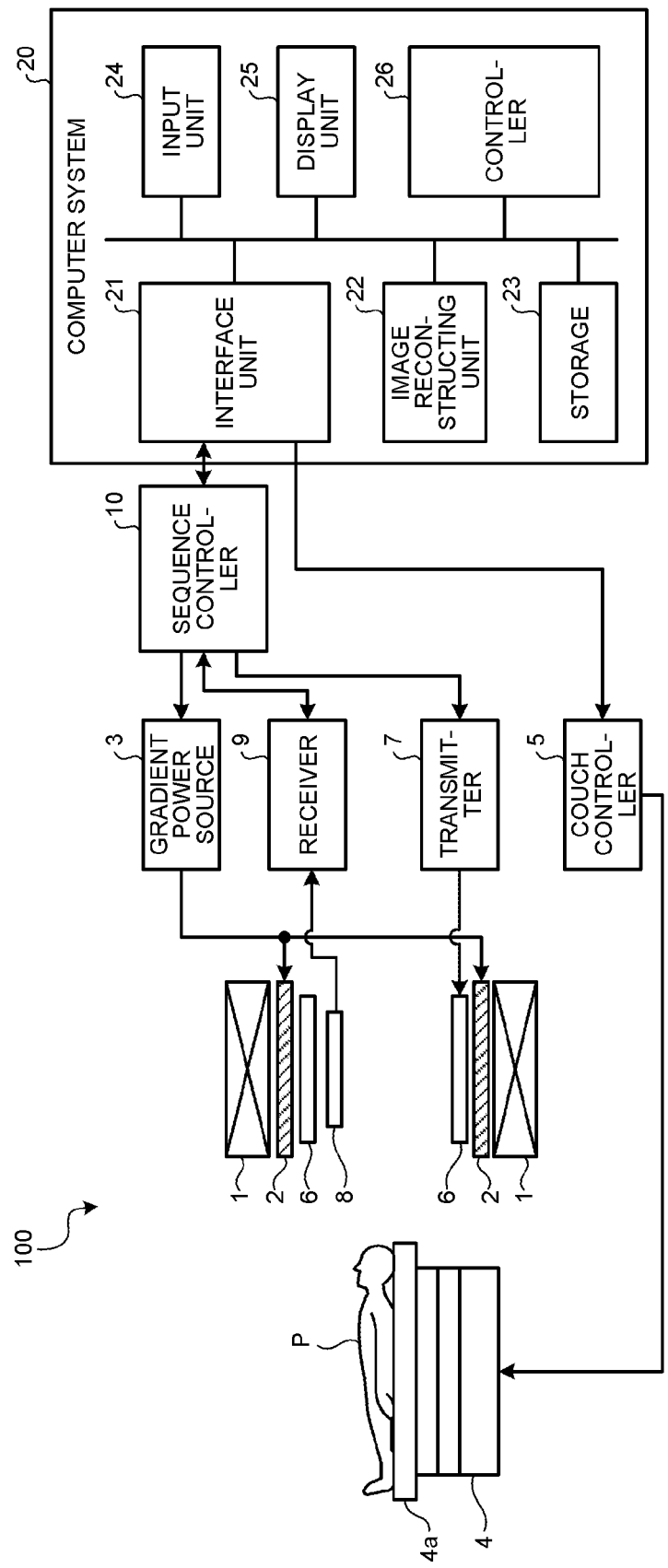
FIG. 1 is a diagram of an MRI apparatus according to an embodiment.

FIG. 1 is a diagram of the MRI apparatus according to the present embodiment. As shown in FIG. 1, an MRI apparatus 100 includes a static magnetic field magnet 1, a gradient coil 2, a gradient power source 3, a couch 4, a couch controller 5, a transmission Radio Frequency (RF) coil 6, a transmitter 7, a receiving RF coil 8, a receiver 9, a sequence controller 10, and a computer system 20.

The static magnetic field magnet 1 is a magnet formed in the shape of a hollow circular cylinder and generates a uniform static magnetic field in the space on the inside thereof. The static magnetic field magnet 1 may be configured by using, for example, a permanent magnet or a superconductive magnet.

The gradient coil 2 is a coil formed in the shape of a hollow circular cylinder and is disposed on the inside of the static magnetic field magnet 1. The gradient coil 2 is formed by combining three coils corresponding to x-, y-, and z-axes that are orthogonal to one another. These three coils individually receive a supply of electric current from the gradient power source 3 (explained later) and generate gradient magnetic fields of which the magnetic field intensities change along the x-, y-, and z-axes. It is assumed that the z-axis direction is the same as the direction of the static magnetic field. The gradient power source 3 supplies the electric current to the gradient coil 2.

In this situation, the gradient magnetic fields on the x-, y-, and z-axes that are generated by the gradient coil 2 correspond to, for example, a slice-selecting-purpose gradient magnetic field Gss, a phase-encoding-purpose gradient magnetic field Gpe, and a read-out-purpose gradient magnetic field Gro, respectively. The slice-selecting-purpose gradient magnetic field Gss is used for determining an imaging slice in an arbitrary manner. The phase-encoding-purpose gradient magnetic field Gpe is used for changing the phase of a magnetic resonance signal according to a spatial position. The read-out-purpose gradient magnetic field Gro is used for changing the frequency of a magnetic resonance signal according to a spatial position.

The couch 4 includes a couchtop 4a on which a subject P is placed. Under control of the couch controller 5 (explained later), while the subject P is placed thereon, the couchtop 4a is inserted into the hollow (i.e., an opening for imaging) of the gradient coil 2. Normally, the couch 4 is provided so that the longitudinal direction thereof extends parallel to the central axis of the static magnetic field magnet 1. The couch controller 5 is a device configured to control the couch 4 under control of a controller 26 and is configured to drive the couch 4 so that the couchtop 4a moves in longitudinal directions and in up-and-down directions.

The transmitting RF coil 6 is disposed on the inside of the gradient coil 2 and generates a Radio Frequency (RF) pulse (a radio frequency magnetic field pulse) by using a radio frequency pulse current supplied from the transmitter 7. The transmitter 7 supplies the radio frequency pulse current corresponding to a Larmor frequency to the transmitting RF coil 6. The receiving RF coil 8 is disposed on the inside of the gradient coil 2 and receives magnetic resonance signals emitted from the subject P due to an influence of the radio frequency pulse described above. When having received the magnetic resonance signals, the receiving RF coil 8 outputs the received magnetic resonance signals to the receiver 9.

The receiver 9 generates Magnetic Resonance (MR) signal data on the basis of the magnetic resonance signals being output from the receiving RF coil 8. The receiver 9 generates the MR signal data by applying a digital conversion to the magnetic resonance signals being output from the receiving RF coil 8. The MR signal data is arranged in a k-space while being kept in correspondence with information about spatial frequencies in a phase encoding direction, a read-out direction, and a slice direction, by the slice-selecting-purpose gradient magnetic field Gss, the phase-encoding-purpose gradient magnetic field Gpe, and the read-out-purpose gradient magnetic field Gro described above. Further, when having generated the MR signal data, the receiver 9 transmits the generated MR signal data to the sequence controller 10.

The sequence controller 10 performs a scan on the subject P, by driving the gradient power source 3, the transmitter 7, and the receiver 9, on the basis of sequence execution data transmitted from the computer system 20. In this situation, the sequence execution data is information that defines a pulse sequence indicating a procedure for performing the scan on the subject P such as the following: the intensity of the power source to be supplied by the gradient power source 3 to the gradient coil 2 and the timing with which the power source is to be supplied; the strength of the RF signal to be transmitted by the transmitter 7 to the transmitting RF coil 6 and the timing with which the RF signal is to be transmitted; and the timing with which the magnetic resonance signals are to be detected by the receiver 9. After driving the gradient power source 3, the transmitter 7, and the receiver 9 on the basis of the sequence execution data, when the MR signal data has been transmitted thereto from the receiver 9, the sequence controller 10 transfers the MR signal data to the computer system 20.

The computer system 20 exercises overall control of the MRI apparatus 100. For example, by driving the functional units included in the MRI apparatus 100, the computer system 20 performs the scan on the subject P and performs an image reconstructing process. The computer system 20 includes an interface unit 21, an image reconstructing unit 22, storage 23, an input unit 24, a display unit 25, and the controller 26.

The interface unit 21 controls inputs and outputs of various types of signals transmitted to and received from the sequence controller 10. For example, the interface unit 21 transmits the sequence execution data to the sequence controller 10 and receives the MR signal data from the sequence controller 10. When having received pieces of MR signal data, the interface unit 21 stores the pieces of MR signal data into the storage 23, while keeping the pieces of MR signal data in correspondence with different subjects P.

The image reconstructing unit 22 generates spectrum data or image data of a desired nuclear spin inside the subject P, by applying a post-processing process i.e., a reconstructing process such as a Fourier transform process to the MR signal data stored in the storage 23. Further, the image reconstructing unit 22 stores the generated spectrum data or image data into the storage 23 so that the stored data is kept in correspondence with each subject P.

The storage 23 stores therein various types of data and various types of computer programs that are necessary for processes performed by the controller 26 (explained later). For example, the storage 23 stores therein the MR signal data received by the interface unit 21, the spectrum data or the image data generated by the image reconstructing unit 22, and the like, while keeping the data in correspondence with each subject P. For example, the storage 23 is configured by using a semiconductor memory element such as a Random Access Memory (RAM), a Read-Only Memory (ROM), or a flash memory, or a storage device such as a hard disk, or an optical disk.

The input unit 24 receives various types of instructions and inputs of information from an operator. The input unit 24 may be configured by using, as appropriate, any of pointing devices such as a mouse and a trackball, selecting devices such as a mode changing switch, and input devices such as a keyboard.

Under control of the controller 26, the display unit 25 displays various types of information such as the spectrum data or the image data. The display unit 25 may be configured by using a display device such as a liquid crystal display device.

The controller 26 includes a Central Processing Unit (CPU), a memory, and the like (not shown) and is configured to exercise overall control of the MRI apparatus 100. For example, the controller 26 controls scans by generating various types of sequence execution data on the basis of imaging conditions input from the operator via the input unit 24 and transmitting the generated sequence execution data to the sequence controller 10. Further, when the MR signal data has been transmitted from the sequence controller 10 as a result of a scan, the controller 26 controls the image reconstructing unit 22 so as to reconstruct an image on the basis of the MR signal data.

A configuration of the MRI apparatus 100 has thus been explained. The MRI apparatus 100 configured as described above has a function of detecting, when at least ones of intervertebral discs and vertebral bodies of a subject are target sites, position information indicating a position and an orientation of each of the plurality of target sites included in the spine, on the basis of an image on which the spine of the subject is visualized. Conventionally, when such a function is used, there have been some situations where the detection of the intervertebral discs or the vertebral bodies fails in a region where the contrast of the intervertebral discs or the vertebral bodies is weak in the detection-purpose image.

To cope with these situations, the MRI apparatus 100 according to the present embodiment detects a detection failure region including a target site of which the detection of the position information failed from among the plurality of target sites, on the basis of the detected position information, and sets an imaging condition used for imaging of an imaging region set so as to include the detection failure region. With this arrangement, even if there is a region in which the detection of the intervertebral discs or the vertebral bodies failed, it is possible to easily obtain a diagnosis image of such a region.

Next, the MRI apparatus 100 configured as described above will be explained more specifically. In the following description, an example will be explained in which the target sites are intervertebral discs.

The MRI apparatus 100 according to the present embodiment includes a specifying unit and an acquiring unit. The specifying unit specifies, on the basis of a detection result of target sites of a subject detected from an image on which the target sites are visualized, a first region and a second region which is different from the first region on the image. The acquiring unit acquires data of the second region by using an imaging condition which is different from an imaging condition on an imaging slice and used for acquiring data of the first region.

Further, the MRI apparatus 100 according to the present embodiment further includes a generating unit that generates a desired slice image including the target site in the second region, by performing an image processing on a plurality of imaging slices acquired from the second region.

Further, according to the present embodiment, as for the first region, the acquiring unit acquires data of an imaging slice set with the target site in the first region, by using a 2D sequence, and as for the second region, the acquiring unit acquires data of an imaging region set in a range that includes the second region, by using a 3D sequence.

Further, according to the present embodiment, the acquiring unit acquires data of an imaging region set in a range that includes both the first region and the second region, by using a 3D sequence.

Further, according to the present embodiment, as for the first region, the acquiring unit acquires data of an imaging slice set with the target site in the first region, by using a 2D sequence, and as for the second region, the acquiring unit acquires data of each of a plurality of imaging slices set in a range that includes the second region, by using a 2D sequence.

Further, according to the present embodiment, the acquiring unit acquires the data related to the second region by using the 2D sequence that is different from the 2D sequence used for acquiring the data related to the first region, in regard to at least one of a quantity, a thickness, and a gap of imaging slices.

Further, the MRI apparatus 100 according to the present embodiment further includes a display controlling unit that causes a display unit to display a slice image corresponding to the first region and a slice image corresponding to the second region in an order according to subject coordinates, which are coordinates related to the subject.

Further, according to the present embodiment, the image on which the target sites of the subject are visualized is an image on which the spine of the subject is visualized, and the target sites are at least ones of intervertebral discs and vertebral bodies of the subject.

Further, according to the present embodiment, the specifying unit specifies a region in which the detection of the target sites was successful as the first region, and the specifying unit specifies a region in which the detection of the target sites failed as the second region.

Further, according to the present embodiment, with respect to the target sites detected from the image, the specifying unit calculates a distance between target sites for each of sets of adjacent target sites and, when there is at least one set of which the calculated distance is longer than a reference value, the specifying unit specifies a range positioned between the target sites in the set as the second region.

Further, the MRI apparatus 100 according to the present embodiment includes a detecting unit, a specifying unit, and an acquiring unit. The detecting unit detects a target site of a subject from an image on which the target site is visualized. The specifying unit specifies, when the detection of the target site failed, a detection failure region including the target site on the image. The acquiring unit acquires data of the detection failure region by using a 3D sequence.

In the present embodiment, the 2D sequence is a pulse sequence used for acquiring two-dimensional slice images, by performing encoding processes in the phase encoding direction and the read-out direction, with respect to one or more positions along the slice direction. In contrast, the 3D sequence is a pulse sequence used for acquiring three-dimensional volume data by performing encoding processes not only in the phase encoding direction and the read-out direction, but also in the slice direction.

Figure 2:
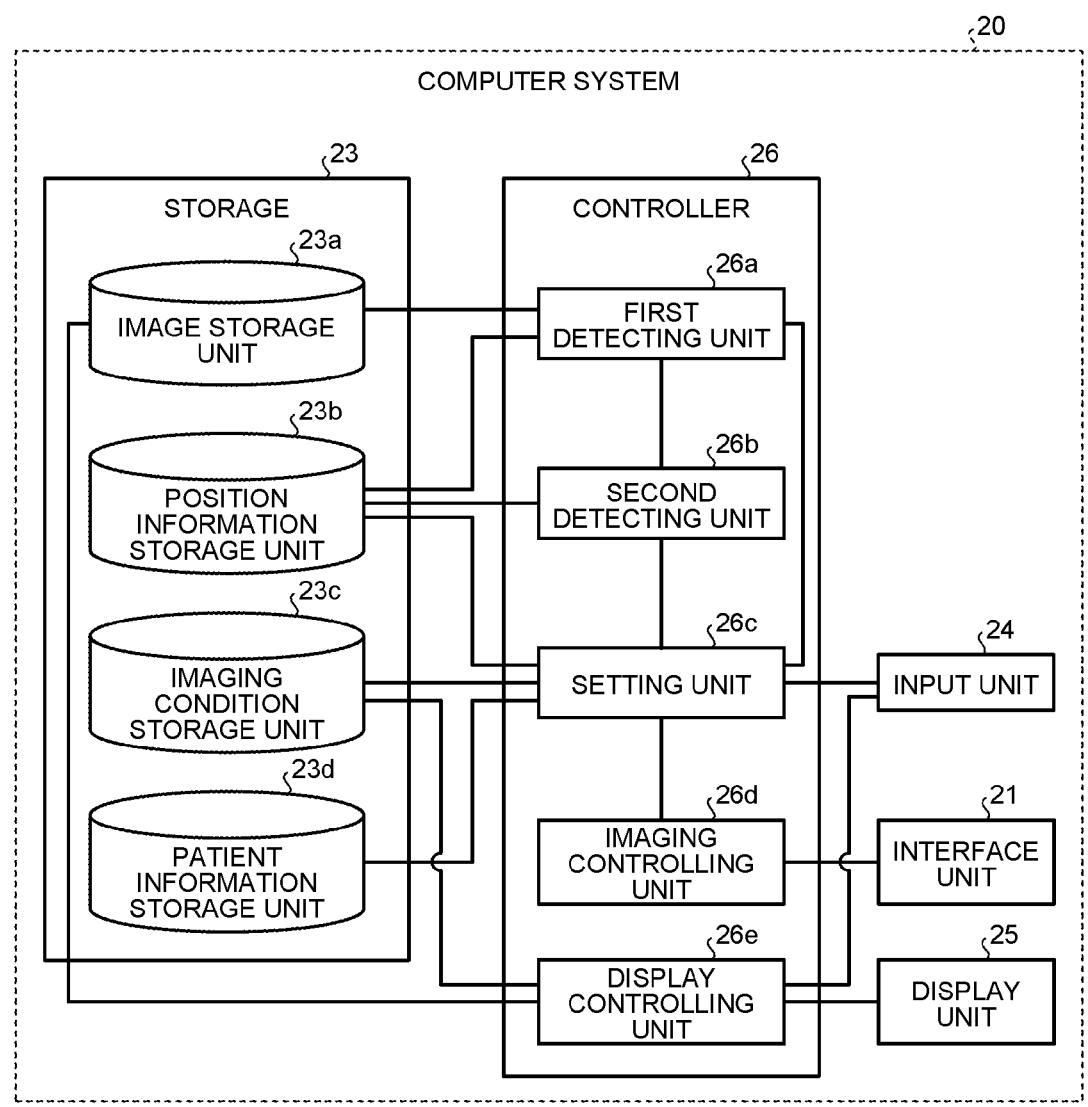
FIG. 2 is a functional block diagram of a detailed configuration of the MRI apparatus according to the present embodiment.

FIG. 2 is a functional block diagram of a detailed configuration of the MRI apparatus 100 according to the present embodiment. Of the functional units included in the computer system 20 shown in FIG. 1, FIG. 2 illustrates the interface unit 21, the storage 23, the input unit 24, the display unit 25, and the controller 26.

As shown in FIG. 2, the storage 23 includes an image storage unit 23a, a position information storage unit 23b, an imaging condition storage unit 23c, and a subject information storage unit 23d.

The image storage unit 23a stores therein the image data generated by the image reconstructing unit 22. For example, the image storage unit 23a stores therein a detection-purpose sagittal image on which the spine of the subject P is visualized. The detection-purpose sagittal image in this situation is a sagittal image that is parallel to a sagittal plane including intervertebral discs and the spinal canal of the subject and that includes at least intervertebral discs. For example, the detection-purpose sagittal image is taken by using a sequence (e.g., a Field Echo [FE]-based sequence) that is able to image the intervertebral discs with higher signal values than those of the vertebral bodies.

In this situation, the detection-purpose image may be any of various types of images. For example, the detection-purpose image may be an image suitable for a detecting process performed for detecting the target site and is an image taken by executing a specific sequence determined in accordance with the detecting process. Alternatively, the detection-purpose image may be an arbitrary image that is generated during a time period, when a plurality of imaging processes are repeated to obtain a diagnosis-purpose image. For example, when a procedure is repeatedly performed in which an image taken at an arbitrary point in time is used as a position determining image for determining the imaging position of the next image to be taken, the position determining image may be used as the detection-purpose image. In yet another example, it is acceptable to generate one slice image from a plurality of slice images or a volume data obtained by imaging an imaging region set in a large area of the subject and to use the slice image as the detection-purpose image.

The position information storage unit 23b stores therein the position information of the target sites detected on the basis of the image on which the spine of the subject P is visualized. The position information in this situation is information indicating the positions and the orientations of the target sites. For example, the position information storage unit 23b stores therein stores therein the position information of each of the plurality of intervertebral discs detected on the basis of the detection-purpose sagittal image stored in the image storage unit 23a. For example, as the position information of each of the intervertebral discs, the position information storage unit 23b stores therein a first vector indicating the orientation of the intervertebral disc and coordinates indicating the starting position of the first vector or a second vector (a vector starting from a predetermined reference position).

The imaging condition storage unit 23c stores therein, for each of the protocols that are determined in accordance with target sites of imaging and/or purposes of imaging, an imaging condition related to a corresponding one of various types of imaging methods and a corresponding one of various types of pulse sequences. The imaging condition in this situation includes various types of imaging parameters such as a repetition time (TR), an echo time (TE), the number of matrices, and the size (the length and the width) and the thickness of an imaging slice. Further, the imaging condition also includes the type, the number, and the order of pre-pulses such as a fat suppressing pulse and an inversion pulse, as well as the order in which images of imaging slices are taken.

For example, as imaging conditions corresponding to a protocol for imaging of intervertebral discs, the imaging condition storage unit 23c stores therein an imaging condition for imaging the detection-purpose sagittal image and an imaging condition for imaging of imaging slices that are set with the intervertebral discs while using a two-dimensional (2D) sequence. In this situation, the imaging condition for the 2D sequence includes the number of intervertebral discs serving as imaging targets and the positions and the orientations of the imaging slices. Further, when imaging slices are set in units of slabs (which may be referred to as slice groups) each of which is represented by a plurality of imaging slices that are arranged along the thickness direction thereof, the imaging condition includes the number of imaging slices to be included in a single slab and the gap between the imaging slices.

The subject information storage unit 23d stores therein subject information related to subject s. For example, the subject information storage unit 23d stores therein, for each subject, subject information including identification information, the name, the age, the height, and the weight of the subject.

Further, the controller 26 includes the specifying unit, the acquiring unit, the generating unit, and a display controlling unit. In the present embodiment, the controller 26 includes a first detecting unit 26a and a second detecting unit 26b, as the specifying unit. Further, the controller 26 includes a setting unit 26c and an imaging controlling unit 26d, as the acquiring unit. In addition, the controller 26 includes a display controlling unit 26e as the generating unit and the display controlling unit.

The first detecting unit 26a is configured to detect, when at least ones of intervertebral discs and vertebral bodies of a subject are target sites, the position information indicating the position and the orientation of each of the plurality of target sites included in the spine, on the basis of an image on which the spine of the subject is visualized.

More specifically, by analyzing the image being stored in the image storage unit 23a and on which the spine of the subject is visualized, the first detecting unit 26a detects, for each of the plurality of target sites included in the spine, the position information indicating the position and the orientation of the target site. After that, the first detecting unit 26a stores the detected position information of the intervertebral discs into the position information storage unit 23b.

For example, the first detecting unit 26a reads the detection-purpose sagittal image on which the spine of the subject P is visualized from the image storage unit 23a and detects the position information of the intervertebral discs included in the spine visualized in the detection-purpose sagittal image, on the basis of the read detection-purpose sagittal image. In this situation, the method implemented by the first detecting unit 26a to detect the intervertebral discs may be any of various types of methods.

For example, the first detecting unit 26a may detect the position information of the intervertebral discs by implementing a method that uses a plurality of sagittal images of the subject. According to this method, the first detecting unit 26a extracts a spine region from each of the plurality of sagittal images each of which is parallel to a sagittal plane including intervertebral discs and the spinal canal of the subject and each of which includes at least intervertebral discs. Further, the first detecting unit 26a extracts a two-dimensional intervertebral disc region from each of the extracted plurality of spine regions. After that, on the basis of the extracted plurality of two-dimensional intervertebral disc regions, the first detecting unit 26a extracts a three-dimensional intervertebral disc region that spreads over a plurality of the sagittal images.

In the description above, the example is explained in which the first detecting unit 26a detects the intervertebral disc information on the basis of the detection-purpose sagittal image; however, possible embodiments are not limited to this example. For instance, the first detecting unit 26a may detect the intervertebral disc information on the basis of various types of images taken for diagnosis purposes. In other words, it is possible to use any of various types of images as long as the image includes intervertebral discs and the spinal canal of the subject and includes at least intervertebral discs.

Further, on the basis of the detected position information, the first detecting unit 26a detects, for each of the target sites of which the detection of the position information was successful, a detection success region indicating an imaging slice set with the target site. At that time, the first detecting unit 26a sets the size and the thickness of each of the detection success regions, on the basis of the 2D sequence imaging condition for performing an intervertebral disc imaging process stored in the imaging condition storage unit 23c. After that, the first detecting unit 26a sends information indicating the detected detection success regions to the setting unit 26c.

On the basis of the position information detected by the first detecting unit 26a, the second detecting unit 26b is configured to detect, if any, a detection failure region including the target site of which the detection of the position information failed, from among the plurality of target sites included in the spine of the subject.

More specifically, with respect to the plurality of target sites of which the position information was detected by the first detecting unit 26a, the second detecting unit 26b calculates the distance between the target sites, for each of the sets made up of two target sites positioned adjacent to each other. Further, if there is at least one set of which the calculated distance is longer than a reference value, the second detecting unit 26b detects the range positioned between the target sites in the set as the detection failure region. In this situation, if at least one detection failure region has been detected, the second detecting unit 26b sends information indicating the detected detection failure region to the setting unit 26c.

For example, on the basis of the position information of the intervertebral discs detected by the first detecting unit 26a, the second detecting unit 26b calculates a distance between intervertebral discs for each of the sets made up of two intervertebral discs positioned adjacent to each other (hereinafter, "adjacently-positioned intervertebral discs"), with respect to the plurality of intervertebral discs of which the detection information was detected. At that time, for example, the second detecting unit 26b smoothly connects the detected positions of the intervertebral discs with one another by using an approximation curve by performing a spline interpolation process or the like and calculates the distance between the intervertebral discs for each of the sets made up of adjacently-positioned intervertebral discs along the approximation curve. After that, on the basis of the reference value set in advance, the second detecting unit 26b evaluates the calculated distance, for each of the sets made up of adjacently-positioned intervertebral discs. At that time, for example, for each of the sets made up of adjacently-positioned intervertebral discs, the second detecting unit 26b compares the calculated distance with the reference value and judges if there is any set of which the distance is longer than the reference value. After that, if there is at least one set of which the distance is determined to be longer than the reference value, the second detecting unit 26b detects the range positioned between the intervertebral discs in the set as the detection failure region.

In the description above, the example is explained in which the second detecting unit 26b evaluates the distances between the intervertebral discs by using the reference value set in advance; however, the reference value used for the evaluation is not limited to the one in this example. For instance, the second detecting unit 26b may use a distance between intervertebral discs calculated from the height of the subject as a reference value. In that situation, for example, the second detecting unit 26b refers to the subject information stored in the subject information storage unit 23d and obtains the height of the subject who is the imaging target. After that, by using a calculation formula expressing a typical relationship between one's height and the distance between intervertebral discs that is defined on the basis of anatomical aspect in advance, the second detecting unit 26b calculates a distance between intervertebral discs from the height of the subject and uses the calculated distance as the reference value.

The setting unit 26c is configured to set the imaging condition used for imaging the imaging region set in a range that includes the detection failure region detected by the second detecting unit 26b.

More specifically, if the second detecting unit 26b detected no detection failure region, the setting unit 26c sets an imaging condition used for imaging, by using a 2D sequence, of the imaging slices set in the detection success regions, with respect to the detection success regions detected by the first detecting unit 26a. On the contrary, if the second detecting unit 26b detected at least one detection failure region, the setting unit 26c sets an imaging condition by using one of the three modes explained below.

For example, the setting unit 26c may set the imaging condition by using a mode selected by the operator. In that situation, the modes that can be implemented by the setting unit 26c are, for example, input by the operator as a part of imaging conditions and stored into the storage 23. After that, the setting unit 26c refers to the modes stored in the storage 23 and judges in which mode the imaging condition is to be set. As for the timing with which the mode is set by the operator, the mode may be set prior to an imaging planning process or during an imaging planning process.

First, in a first mode, the setting unit 26c sets an imaging condition used for imaging, by using a 2D sequence, of the imaging slices set in the detection success regions, with respect to the detection success regions detected by the first detecting unit 26a. Further, the setting unit 26c sets an imaging condition used for imaging, by using a 3D sequence, of the imaging region set in a range that includes the detection failure region, with respect to the detection failure region detected by the second detecting unit 26b.

Figure 3:
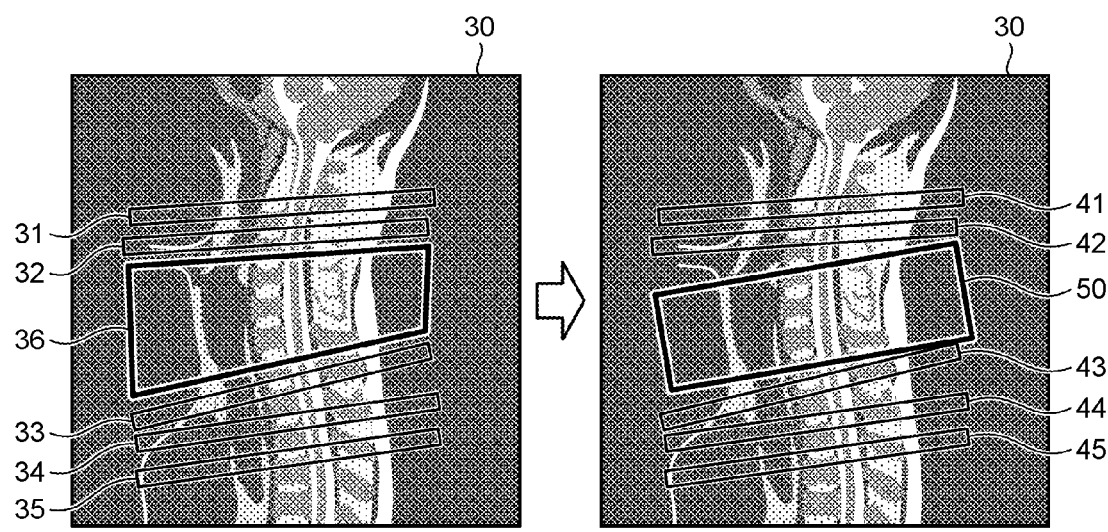
FIG. 3 is a drawing of an example in a first mode implemented by a setting unit according to the present embodiment.

FIG. 3 is a drawing of an example in the first mode implemented by the setting unit 26c according to the present embodiment. For example, as illustrated on the left side of FIG. 3, let us assume that the first detecting unit 26a sequentially detected five detection success regions 31 to 35 arranged starting from the head side, from a detection-purpose sagittal image 30 on which the spine of the subject is visualized. Further, let us assume that the second detecting unit 26b detected a detection failure region 36 between the second detection success region 32 and the third detection success region 33 from the head side, which are among the detection success regions 31 to 35.

In that situation, in the first mode, as illustrated on the right side of FIG. 3, for example, with respect to the detection success region 31, the setting unit 26c sets a slab 41 including imaging slices of which the quantity is determined in the imaging condition, in such a manner that the slab 41 extends parallel to one of the intervertebral discs and includes the one intervertebral disc. Further, for each of the detection success regions 32 to 35, the setting unit 26c similarly sets slabs 42 to 45. In that situation, on the basis of the position information of the intervertebral discs detected by the first detecting unit 26a, the setting unit 26c calculates the positions and the orientations of the imaging slices included in the slabs 41 to 45. After that, the setting unit 26c sets the calculated positions and orientations of the imaging slices into the 2D sequence imaging condition for performing the intervertebral disc imaging process stored in the imaging condition storage unit 23c. Further, with respect to the detection failure region 36, the setting unit 26c sets an imaging region 50 that defines a range covering substantially the entirety of the detection failure region 36 as an imaging target. After that, the setting unit 26c sets an imaging condition used for taking, by using a 3D sequence, data of the imaging region 50.

More specifically, the setting unit 26c generates the imaging condition used for imaging, by using the 3D sequence, of the imaging region 50 and adds the generated imaging condition to the protocol for the intervertebral disc imaging process stored in the imaging condition storage unit 23c. In other words, the setting unit 26c adds a protocol for imaging the imaging region 50 by using the 3D sequence, to the protocol for the intervertebral disc imaging process. At that time, the setting unit 26c sets the size and the orientation of the imaging region 50, on the basis of the information indicating the detection failure region sent thereto from the second detecting unit 26b. Further, the setting unit 26c generates the 3D sequence imaging condition, by conveniently utilizing the 2D sequence imaging condition for performing the intervertebral disc imaging process stored in the imaging condition storage unit 23c. Alternatively, if the imaging condition storage unit 23c has stored therein, in advance, an imaging condition that can serve as a base for the 3D sequence of the intervertebral disc imaging process, the setting unit 26c may generate a 3D sequence imaging condition by setting a size and an orientation of the imaging region 50 into the stored imaging condition.

Next, in a second mode, the setting unit 26c sets an imaging condition used for imaging, by using a 3D sequence, of an imaging region set in a range that includes both the detection success regions detected by the first detecting unit 26a and the detection failure region detected by the second detecting unit 26b.

Figure 4:
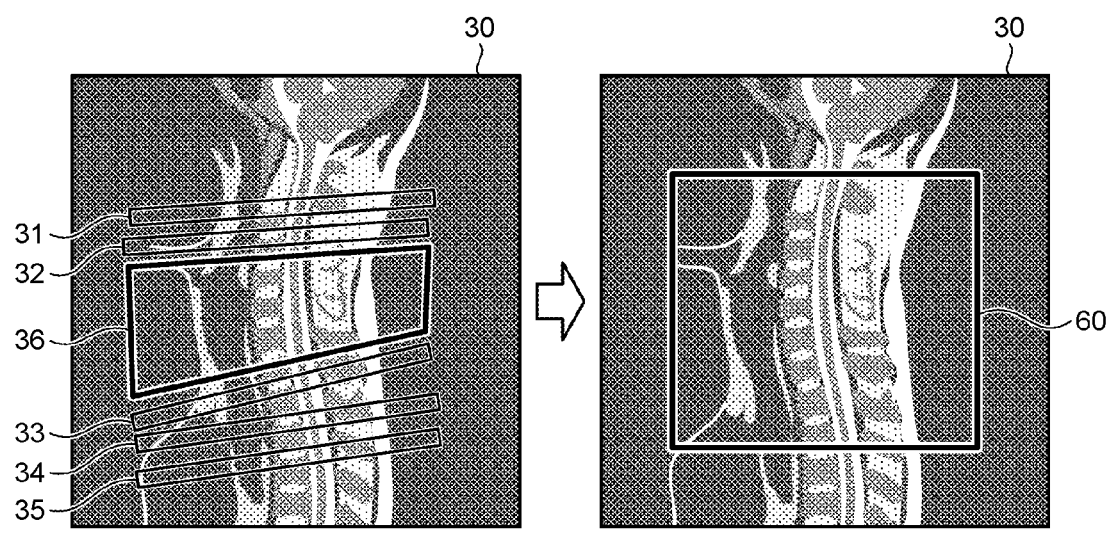
FIG. 4 is a drawing of an example in a second mode implemented by the setting unit according to the present embodiment.

FIG. 4 is a drawing of an example in the second mode implemented by the setting unit 26c according to the present embodiment. In the second mode, as illustrated on the right side of FIG. 4, for example, the setting unit 26c sets an imaging region 60 so as to include both the detection success regions 31 to 35 and the detection failure region 36. After that, the setting unit 26c sets the imaging condition used for taking, by using the 3D sequence, data of the imaging region 60.

More specifically, the setting unit 26c generates the imaging condition used for imaging, by using the 3D sequence, of the imaging region 60 and replaces the 2D sequence imaging condition for performing the intervertebral disc imaging process stored in the imaging condition storage unit 23c, with the generated imaging condition. In other words, the setting unit 26c changes the 2D sequence imaging condition that was set as the protocol for the intervertebral disc imaging process, into the 3D sequence imaging condition. In that situation, on the basis of the position information of the intervertebral discs detected by the first detecting unit 26a and the information indicating the detection failure region sent thereto from the second detecting unit 26b, the setting unit 26c sets the size and the orientation of the imaging region 60. Further, the setting unit 26c generates the 3D sequence imaging condition, by conveniently utilizing the 2D sequence imaging condition for performing the intervertebral disc imaging process stored in the imaging condition storage unit 23c. Alternatively, if the imaging condition storage unit 23c has stored therein, in advance, an imaging condition that can serve as a base for the 3D sequence of the intervertebral disc imaging process, the setting unit 26c may generate a 3D sequence imaging condition by setting a size and an orientation of the imaging region 60 into the stored imaging condition.

Next, in a third mode, with respect to the detection success regions detected by the first detecting unit 26a, the setting unit 26c sets an imaging condition used for imaging, by using a 2D sequence, of the imaging slices set in the detection success regions. Further, with respect to the detection failure region detected by the second detecting unit 26b, the setting unit 26c sets an imaging condition used for imaging, by using a 2D sequence, of each of a plurality of imaging slices set in a range that includes the detection failure region.

Figure 5:
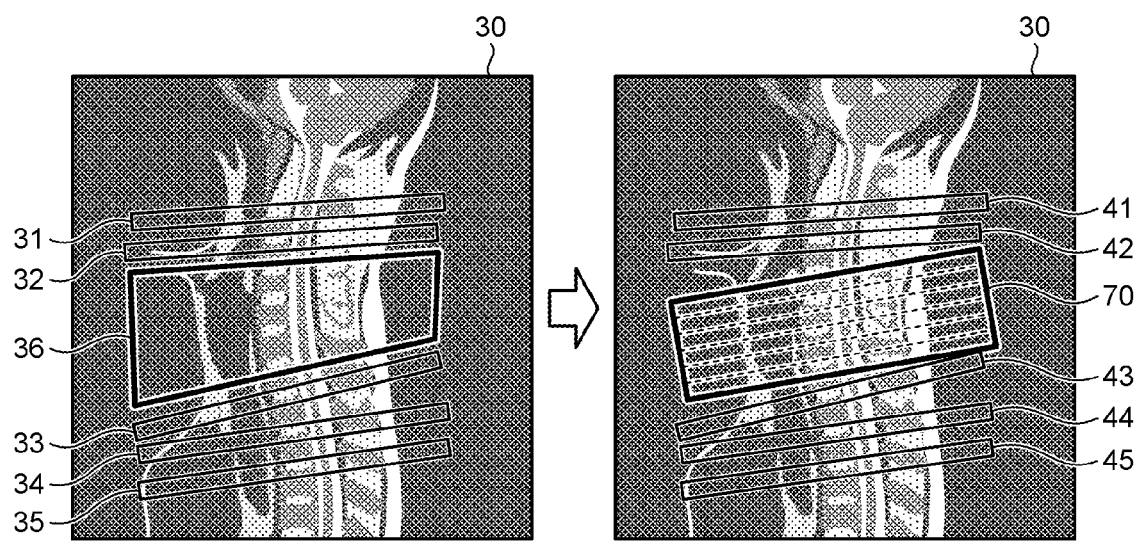
FIG. 5 is a drawing of an example in a third mode implemented by the setting unit according to the present embodiment.

FIG. 5 is a drawing of an example in the third mode implemented by the setting unit 26c according to the present embodiment. In the third mode, as illustrated on the right side of FIG. 5, for example, the setting unit 26c sets the slabs 41 to 45 in correspondence with the detection success regions 31 to 35, like in the first mode. After that, the setting unit 26c sets the positions and the orientations of the imaging slices included in the slabs 41 to 45, into the 2D sequence imaging condition for performing the intervertebral disc imaging process stored in the imaging condition storage unit 23c. Further, with respect to the detection failure region 36, the setting unit 26c sets an imaging region 70 including a plurality of imaging slices, in a range covering substantially the entirety of the detection failure region 36. After that, the setting unit 26c sets the imaging condition used for imaging, by using the 2D sequence, of each of the plurality of imaging slices included in the imaging region 70.

More specifically, the setting unit 26c further sets the positions and the orientations of the imaging slices and the quantity of the imaging slices included in the imaging region 70, into the 2D sequence imaging condition for performing the intervertebral disc imaging process stored in the imaging condition storage unit 23c, as a slab serving as an imaging target. In other words, without changing the type of the sequence, the setting unit 26c changes the imaging condition for the protocol of the 2D sequence, so that the images of both the detection success regions and the detection failure region are taken. In that situation, the setting unit 26c calculates the positions and the orientations of the imaging slices and the quantity of the imaging slices included in the imaging region 70, on the basis of the information indicating the detection failure region sent thereto from the second detecting unit 26b and the 2D sequence imaging condition for performing the intervertebral disc imaging process stored in the imaging condition storage unit 23c. In this situation, the setting unit 26c calculates the quantity to be as many imaging slices as to cover the detection failure region 36, without changing the thickness and the gap of the imaging slices included in the 2D sequence imaging condition.

Alternatively, for the purpose of keeping the image resolution constant, the setting unit 26c may change only the gap, without changing the thickness of the imaging slices. For example, the setting unit 26c may set the gap to zero, without changing the thickness of the imaging slices. In this situation, setting information defining how the thickness and the gap of the imaging slices are to be set is, for example, input by the operator as a part of the imaging condition and stored in the storage 23. After that, the setting unit 26c refers to the setting information stored in the storage 23 and determines the quantity of the imaging slices by changing the thickness and the gap of the imaging slices as appropriate.

After that, the setting unit 26c stores, for each of medical examinations, the information indicating the detection success regions sent thereto from the first detecting unit 26a and the information indicating the detection failure region sent thereto from the second detecting unit 26b, into the imaging condition storage unit 23c. In this situation, the information indicating the detection success regions and the information indicating the detection failure region include coordinates indicating the positions of the regions. These pieces of information are used by the display controlling unit 26e, when determining the order in which the slice images are to be displayed (explained later).

The imaging controlling unit 26d is configured to take one or more images of an imaging target on the basis of the imaging condition set by the setting unit 26c. For example, on the basis of the protocol for the intervertebral disc imaging process stored in the imaging condition storage unit 23c, the imaging controlling unit 26d generates sequence execution data for executing a sequence according to the protocol. After that, the imaging controlling unit 26d causes the intervertebral disc imaging process to be executed, by transmitting the generated sequence execution data to the sequence controller 10.

The display controlling unit 26e is configured to cause the display unit 25 to display a plurality of slice images taken on the basis of the imaging condition set by the setting unit 26c, in an order according to subject's coordinates, which are coordinates related to the subject.

More specifically, the display controlling unit 26e receives, via the input unit 24, an instruction from the operator indicating that the slice images of the target sites taken during a medical examination of the diagnosis target should sequentially be displayed. When having received the instruction, the display controlling unit 26e refers to the imaging condition storage unit 23c and obtains the information indicating the detection success regions and the detection failure region detected in the medical examination specified by the operator. After that, on the basis of the coordinates indicating the positions of the regions, the display controlling unit 26e determines the order in which the slice images corresponding to the regions are to be displayed, so that the order is in accordance with the subject's coordinates. For example, the display controlling unit 26e determines the display order so that the slice images are displayed in an order in the direction from the head toward the feet of the subject.

After that, the display controlling unit 26e causes the display unit 25 to display the slice images corresponding to the regions, according to the determined displayed order. In that situation, the display controlling unit 26e identifies the mode that was used when the imaging condition was set by the setting unit 26c and causes the slice images to be displayed in accordance with the identified mode. For example, by referring to the mode that was input by the operator as a part of the imaging condition and stored in the storage 23, the display controlling unit 26e identifies the mode that was used when the imaging condition was set by the setting unit 26c.

First, an example in which the identified mode is the first mode will be explained. In the first mode, images of the imaging slices set in the detection success regions are taken by using the 2D sequence, whereas an image of the imaging region set in a range that includes the detection failure region is taken by using the 3D sequence. In that situation, the display controlling unit 26e first calculates an interpolation curve connecting the center coordinates of the imaging slices corresponding to the detection success regions. After that, the display controlling unit 26e causes the display unit 25 to display the slice images corresponding to the regions in the display order determined in advance.

In this situation, if a slice image to be displayed corresponds to a detection success region, the display controlling unit 26e reads a corresponding 2D image (a two-dimensional slice image) from the image storage unit 23a and causes the display unit 25 to display the read image. In contrast, if a slice image to be displayed corresponds to the detection failure region, the display controlling unit 26e reads a corresponding 3D image (three-dimensional volume data) from the image storage unit 23a and generates slice images that are orthogonal to the interpolation curve calculated in advance by performing a Multi Planar Reconstruction (MPR) process, on the basis of the read 3D image. In that situation, the display controlling unit 26e generates the slice images at intervals that are equal to the thicknesses of the imaging slices corresponding to the detection success regions. Alternatively, the display controlling unit 26e may use the thicknesses of the imaging slices corresponding to the detection success regions as an initial value of the intervals and change the intervals according to an instruction from the operator. After that, the display controlling unit 26e causes the display unit 25 to display the generated slice images in the order according to the subject's coordinates.

Figure 6:
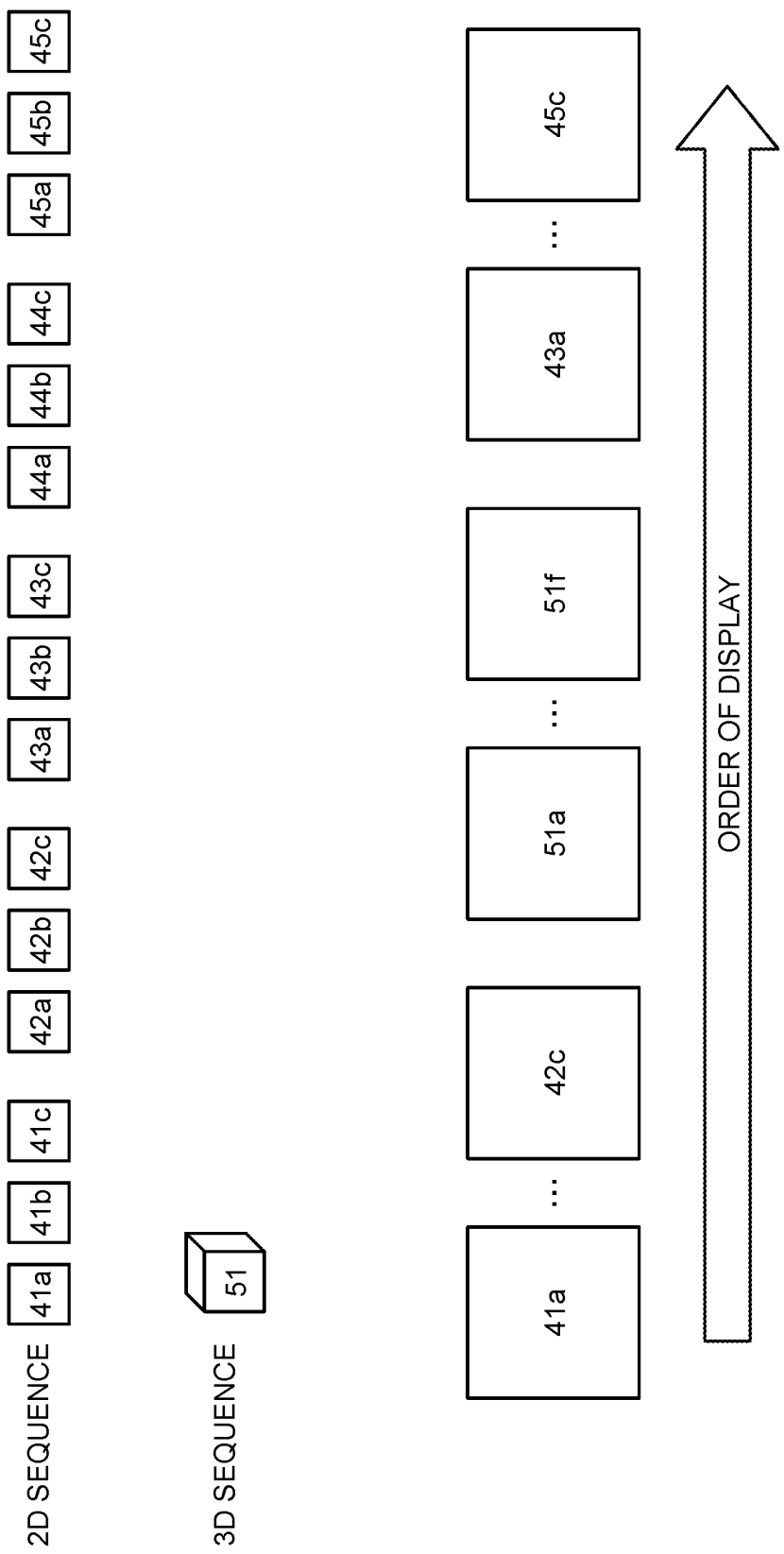
FIG. 6 is a drawing of an example of a display of slice images in the first mode implemented by a display controlling unit according to the present embodiment.

FIG. 6 is a drawing of an example of the display of the slice images in the first mode implemented by the display controlling unit 26e according to the present embodiment. For example, in the example illustrated in FIG. 3, let us assume that, with respect to the slabs 41 to 45 that are set in the detection success regions 31 to 35, three imaging slices are set in each of the slabs. Further, as a result, as illustrated in the top section of FIG. 6, let us assume that, by using a 2D sequence, 2D images 41a to 41c are taken for the slab 41, and 2D images 42a to 42c are taken for the slab 42. In addition, 2D images 43a to 43c are taken for the slab 43, whereas 2D images 44a to 44c are taken for the slab 44, and 2D images 45a to 45c are taken for the slab 45. Furthermore, let us assume that, by using a 3D sequence, a 3D image 51 is taken for the imaging region 50 set in the detection failure region 36.

In that situation, for example, as illustrated in the bottom section of FIG. 6, the display controlling unit 26e first causes 2D images to be sequentially displayed starting with the one positioned closest to the head of the subject, the displayed 2D images namely being the 2D images 41a to 41c corresponding to the detection success region 31 detected in the position closest to the head and the 2D images 42a to 42c corresponding to the detection success region 32 detected in the position next closest to the head after the detection success region 31. After that, on the basis of the 3D image 51 corresponding to the detection failure region 36 detected in the position next closest to the head after the detection success region 32, the display controlling unit 26e generates six slice images 51a to 51f by performing an MPR process and causes the generated slice images to be sequentially displayed, starting with the one positioned closest to the head. Subsequently, the display controlling unit 26e causes 2D images to be sequentially displayed starting with the one positioned closest to the head, the displayed 2D images namely being the 2D images 43a to 43c corresponding to the detection success region 33 detected in the position next closest to the head after the detection failure region 36, the 2D images 44a to 44c corresponding to the detection success region 34 detected in the position next closest to the head after the detection success region 33, and the 2D images 45a to 45c corresponding to the detection success region 35 set in the position next closest to the head after the detection success region 34.

As explained above, if the mode that was used when the imaging condition was set by the setting unit 26c is the first mode, the display controlling unit 26e uses the 2D images taken by using the 2D sequence and the 3D image taken by using the 3D sequence and causes the slice images of the detection success regions and the slice images of the detection failure region to be displayed in the order according to the subject's coordinates. In other words, even if the imaging process was performed with the combination of the plurality of protocols, the display controlling unit 26e causes the slice images of the target sites to be displayed in the order according to the subject's coordinates.

Next, an example in which the identified mode is the second mode will be explained. In the second mode, images of the imaging region set in a range that includes both the detection success regions and the detection failure region are taken by using the 3D sequence. In that situation, the display controlling unit 26e first calculates an interpolation curve connecting the center coordinates of the imaging slices corresponding to the detection success regions. After that, the display controlling unit 26e causes the display unit 25 to display the slice images corresponding to the regions in the display order determined in advance.

In this situation, if a slice image to be displayed corresponds to a detection success region, the display controlling unit 26e reads a corresponding 3D image from the image storage unit 23a, generates slice images in positions corresponding to the detection success region by performing an MPR process on the basis of the read 3D image, and causes the display unit 25 to display the generated slice images. In contrast, if a slice image to be displayed corresponds to the detection failure region, the display controlling unit 26e reads a corresponding 3D image from the image storage unit 23a and generates slice images that are orthogonal to the interpolation curve calculated in advance, by performing an MPR process, on the basis of the read 3D image. In that situation, the display controlling unit 26e generates the slice images at intervals that are equal to the thicknesses of the imaging slices corresponding to the detection success regions. Alternatively, the display controlling unit 26e may use the thicknesses of the imaging slices corresponding to the detection success regions as an initial value of the intervals and change the intervals according to an instruction from the operator. After that, the display controlling unit 26e causes the display unit 25 to display the generated slice images in the order according to the subject's coordinates.

FIG. 7 is a drawing of an example of the display of the slice images in the second mode implemented by the display controlling unit 26e according to the present embodiment. For example, let us assume that, as illustrated in FIG. 4, the imaging region 60 is set so as to include both the detection success regions 31 to 35 and the detection failure region 36. Further, as a result, as illustrated in the top section of FIG. 7, let us assume that, by using a 3D sequence, the 3D image 61 is taken for the imaging region 60.

In that situation, for example, as illustrated in the bottom section of FIG. 7, the display controlling unit 26e first generates slice images from the 3D image 61 by performing an MPR process and causes the generated slice images to be sequentially displayed starting with the one positioned closest to the head of the subject, the displayed slice images namely being three slice images 61a to 61c corresponding to the detection success region 31 detected in the position closest to the head and three slice images 61d to 61f corresponding to the detection success region 32 detected in the position next closest to the head after the detection success region 31. After that, the display controlling unit 26e generates slice images from the 3D image 61 by performing an MPR process and causes the generated slice images to be sequentially displayed starting with the one positioned closest to the head, the displayed slice images namely being six slice images 61g to 61l corresponding to the detection failure region 36 detected in the position next closest to the head after the detection success region 32. Subsequently, the display controlling unit 26e generates slice from the 3D image 61 by performing an MPR process and causes the generated slice images to be sequentially displayed starting with the one positioned closest to the head, the displayed slice images namely being three slice images 61m to 61o corresponding to the detection success region 33 detected in the position next closest to the head after the detection failure region 36, three slice images 61p to 61r corresponding to the detection success region 34 detected in the position next closest to the head after the detection success region 33, and three slice images 61s to 61u corresponding to the detection success region 35 detected in the position next closest to the head after the detection success region 34.

As explained above, if the mode that was used when the imaging condition was set by the setting unit 26c is the second mode, the display controlling unit 26e uses the 3D image taken by using the 3D sequence and causes the slice images of the detection success regions and the slice images of the detection failure region to be displayed in the order according to the subject's coordinates. In other words, even if the protocol for the imaging process is changed from the 2D sequence to the 3D sequence, the display controlling unit 26e causes the slice images of the target sites to be displayed in the order according to the subject's coordinates.

Next, an example in which the identified mode is the third mode will be explained. In the third mode, images of the imaging slices set in the detection success regions are taken by using the 2D sequence, whereas an image of each of the plurality of imaging slices set in a range that includes the detection failure region is taken by using the 2D sequence. In that situation, the display controlling unit 26e first calculates an interpolation curve connecting the center coordinates of the imaging slices corresponding to the detection success regions. After that, the display controlling unit 26e causes the display unit 25 to display the slice images corresponding to the regions in the display order determined in advance.

In this situation, if a slice image to be displayed corresponds to a detection success region, the display controlling unit 26e reads a corresponding 2D image from the image storage unit 23a and causes the display unit 25 to display the read image. In contrast, if a slice image to be displayed corresponds to the detection failure region, the display controlling unit 26e reads a corresponding 2D image from the image storage unit 23a and causes the display unit 25 to display the read image. In that situation, the display controlling unit 26e generates slice images that are orthogonal to the interpolation curve calculated in advance, by performing an MPR process, on the basis of the plurality of 2D images corresponding to the detection failure region. Also, the display controlling unit 26e generates the slice images at intervals that are equal to the thicknesses of the imaging slices corresponding to the detection success regions. Alternatively, the display controlling unit 26e may use the thicknesses of the imaging slices corresponding to the detection success regions as an initial value of the intervals and change the intervals according to an instruction from the operator. As another example, the display controlling unit 26e may read 2D images at intervals that are equal to the thicknesses of the imaging slices corresponding to the detection success regions, from among the plurality of 2D images corresponding to the detection failure region and cause the display unit 25 to display the read 2D images.

Figure 8:
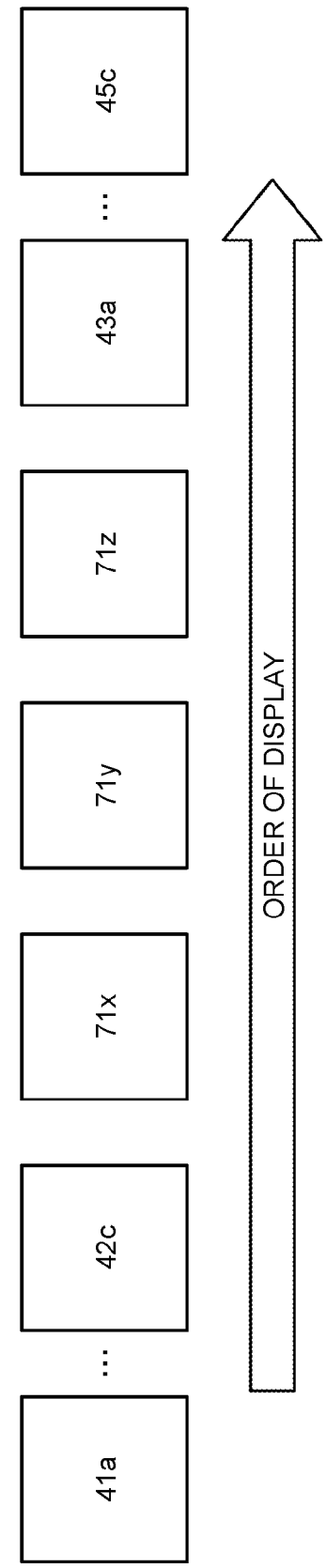
FIG. 8 is a drawing of an example of a display of slice images in the third mode implemented by the display controlling unit according to the present embodiment.

FIG. 8 is a drawing of an example of the display of the slice images in the third mode implemented by the display controlling unit 26e according to the present embodiment. For example, in the example illustrated in FIG. 5, let us assume that, with respect to the slabs 41 to 45 that are set in the detection success regions 31 to 35, three imaging slices are set in each of the slabs and that six imaging slices are set in the imaging region 70 that was set in the detection failure region 36. Further, as a result, as illustrated in the top section of FIG. 8, let us assume that, by using a 2D sequence, the 2D images 41a to 41c are taken for the slab 41, whereas the 2D images 42a to 42c are taken for the slab 42. In addition, the 2D images 43a to 43c are taken for the slab 43, whereas the 2D images 44a to 44c are taken for the slab 44, and the 2D images 45a to 45c are taken for the slab 45. Furthermore, let us assume that, by using a 2D sequence, 2D images 71a to 71f are taken for the imaging region 70 set in the detection failure region 36.

In that situation, for example, as illustrated in the bottom section of FIG. 8, the display controlling unit 26e first causes 2D images to be sequentially displayed starting with the one positioned closest to the head of the subject, the displayed 2D images namely being the 2D images 41a to 41c corresponding to the detection success region 31 detected in the position closest to the head and the 2D images 42a to 42c corresponding to the detection success region 32 detected in the position next closest to the head after the detection success region 31. After that, on the basis of the 2D images 71a to 71f corresponding to the detection failure region 36 detected in the position next closest to the head after the detection success region 32, the display controlling unit 26e generates three slice images 71x to 71z by performing an MPR process and causes the generated slice images to be sequentially displayed, starting with the one positioned closest to the head. Subsequently, the display controlling unit 26e causes 2D images to be sequentially displayed starting with the one positioned closest to the head, the displayed 2D images namely being the 2D images 43a to 43c corresponding to the detection success region 33 detected in the position next closest to the head after the detection failure region 36, the 2D images 44a to 44c corresponding to the detection success region 34 detected in the position next closest to the head after the detection success region 33, and the 2D images 45a to 45c corresponding to the detection success region 35 set in the position next closest to the head after the detection success region 34.

As explained above, if the mode that was used when the imaging condition was set by the setting unit 26c is the third mode, the display controlling unit 26e uses the 2D images taken by using the 2D sequence and causes the slice images of the detection success regions and the slice images of the detection failure region to be displayed in the order according to the subject's coordinates. In other words, even if the 2D sequence imaging condition is changed so as to take the images of both the detection success regions and the detection failure region, the display controlling unit 26e causes the slice images of the target sites to be displayed in the order according to the subject's coordinates.

Figure 9:
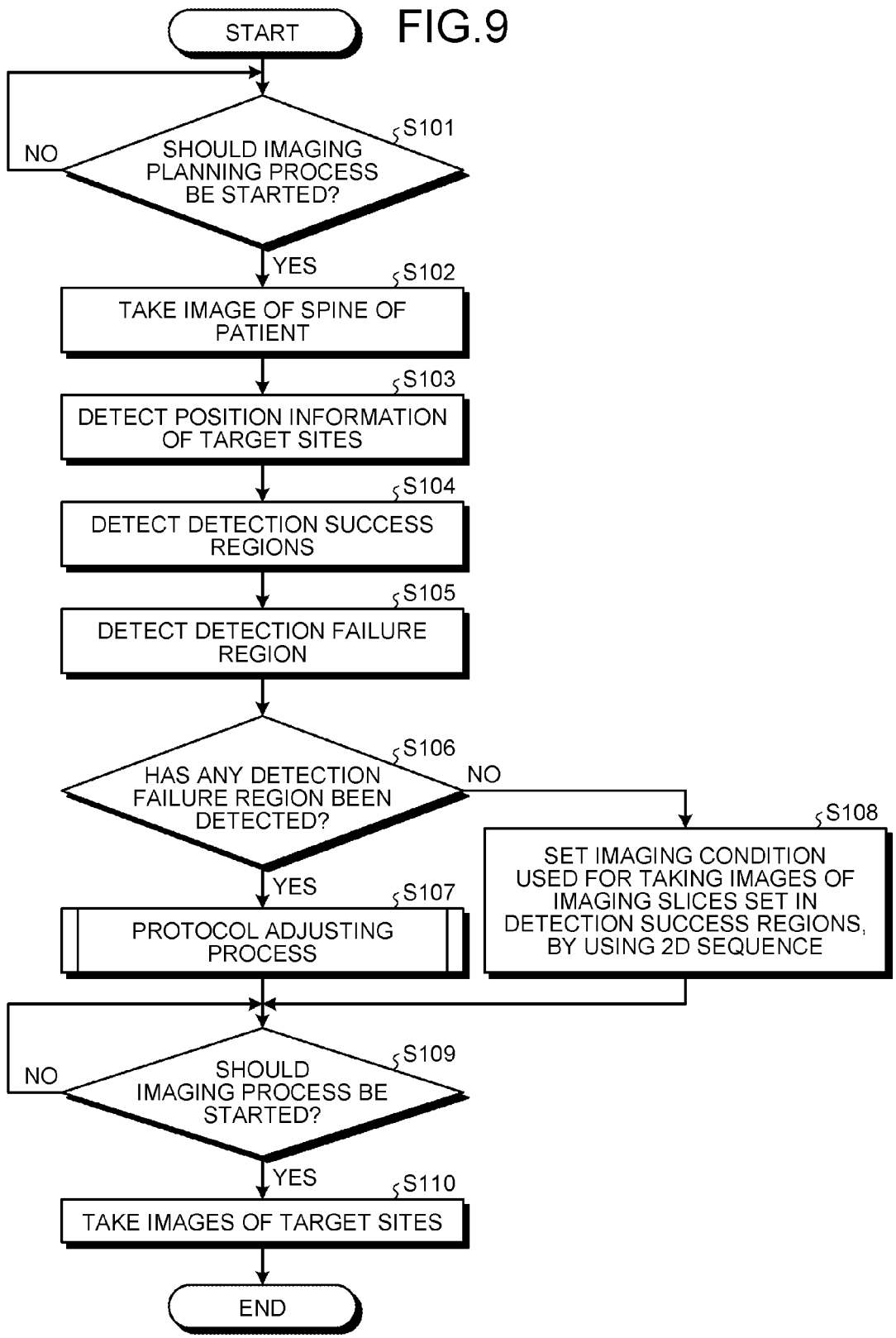
FIG. 9 is a flowchart of a flow in an imaging planning process and an imaging process performed by the MRI apparatus according to the present embodiment.

FIG. 9 is a flowchart of a flow in an imaging planning process and an imaging process performed by the MRI apparatus 100 according to the present embodiment. As illustrated in FIG. 9, in the MRI apparatus 100, when the imaging controlling unit 26d has received an instruction from the operator indicating that an imaging planning process should be started (step S101: Yes), an image rendering the spine of the subject is taken (step S102).

After that, on the basis of the image rendering the spine of the subject, the first detecting unit 26a detects position information of each of the plurality of target sites included in the spine (step S103) and further detects a detection success region for each of the target sites of which the detection of the position information was successful (step S104). Subsequently, on the basis of the position information detected by the first detecting unit 26a, the second detecting unit 26b detects, if any, a detection failure region including the target site of which the detection of the position information failed (step S105).

After that, if the second detecting unit 26b detected at least one detection failure region (step S106: Yes), the setting unit 26c performs a protocol adjusting process (step S107). On the contrary, if the second detecting unit 26b detected no detection failure region (step S106: No), the setting unit 26c sets an imaging condition used for taking images of the imaging slices set in the detection success regions by using a 2D sequence (step S108).

After that, when the imaging controlling unit 26d has received an instruction from the operator indicating that an imaging process should be started (step S109: Yes), images of the imaging target are taken on the basis of the imaging condition set by the setting unit 26c (step S110).

Figure 10:
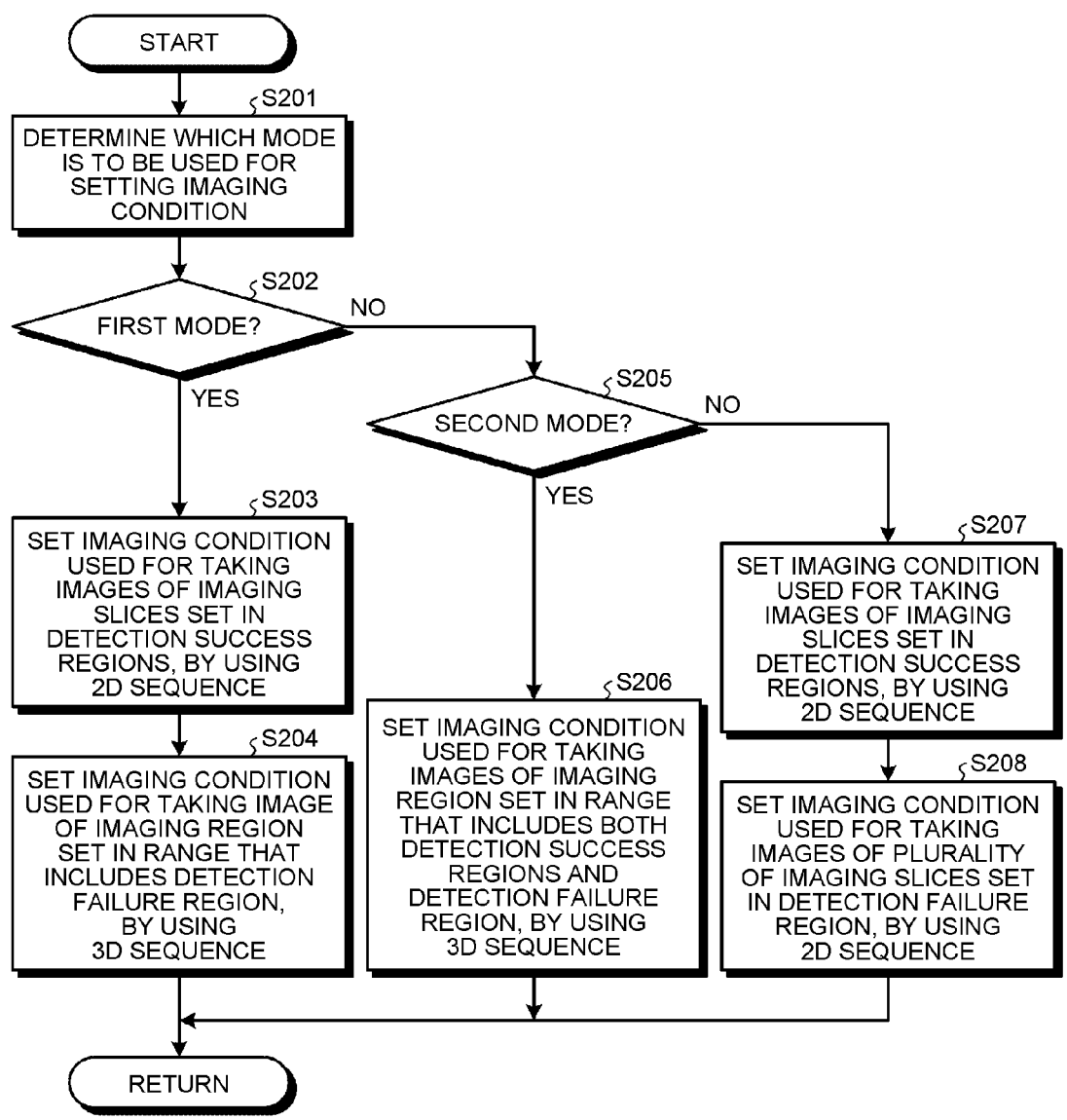
FIG. 10 is a flowchart of a flow in the protocol adjusting process illustrated in FIG. 9.

FIG. 10 is a flowchart of a flow in the protocol adjusting process illustrated in FIG. 9. As illustrated in FIG. 10, the setting unit 26c first judges in which one of the modes (the first, the second, and the third modes) the imaging condition is to be set (step S201).

If the setting unit 26c has determined that an imaging condition is to be set in the first mode (step S202: Yes), the setting unit 26c sets an imaging condition used for taking images of the imaging slices set in the detection success regions by using a 2D sequence (step S203). Further, the setting unit 26c sets an imaging condition used for taking an image of the imaging region set in a range that includes the detection failure region by using a 3D sequence (step S204).

If the setting unit 26c has determined that an imaging condition is to be set in the second mode (step S202: No; step S205: Yes), the setting unit 26c sets an imaging condition used for taking images of the imaging region set in a range that includes both the detection success regions and the detection failure region by using a 3D sequence (step S206).

If the setting unit 26c has determined that an imaging condition is to be set in the third mode (step S205: No), the setting unit 26c sets an imaging condition used for taking images of the imaging slices set in the detection success regions by using a 2D sequence (step S207). Further, the setting unit 26c sets an imaging condition used for taking an image of each of the plurality of imaging slices set in a range that includes the detection failure region by using a 2D sequence (step S208).

As explained above, the MRI apparatus 100 according to the present embodiment is configured to detect the detection failure region including the target site of which the detection of the position information failed and to set the imaging condition used for taking the image of the imaging region set in the range that includes the detection failure region. Thus, according to the present embodiment, even if there is a region where the detection of the intervertebral discs or the vertebral bodies failed, it is possible to easily obtain a diagnosis image of such a region.

Further, the MRI apparatus 100 according to the present embodiment is configured to cause the display unit 25 to display the plurality of slice images taken on the basis of the imaging condition set by the setting unit 26c, in the order according to the subject's coordinates, which are the coordinates related to the subject. Consequently, even if one or more detection failure regions have been detected, the operator is able to view the slice images, while switching between the slice images corresponding to the entire region of the target sites in the order according to the subject's coordinates.

A Modification Example of the Embodiment

Next, modification examples of the embodiment described above will be explained. In the embodiment described above, the example is explained in which, when having received the instruction from the operator indicating that slice images should be displayed, the display controlling unit 26e reads the 2D images corresponding to the detection success regions from the image storage unit 23a and causes the read 2D images to be displayed and generates the slice images from the 3D image corresponding to the detection failure region and causes the generated 3D image to be displayed. In contrast, for example, another arrangement is acceptable in which the image reconstructing unit 22 generates, in advance, display-purpose slice images on the basis of the 2D images and the 3D image, at the point in time when the imaging processes using the 2D sequence and the 3D sequence have been completed. In other words, in the present modification example, the image reconstructing unit 22 corresponds to a generating unit.

More specifically, after generating the 2D and 3D images, the image reconstructing unit 22 refers to the imaging condition storage unit 23c and obtains the information about the detection success regions and the detection failure region that were detected during the medical examination specified by the operator. After that, on the basis of the coordinates indicating the positions of the regions, the image reconstructing unit 22 determines the order in which the slice images corresponding to the regions are to be generated so that the order is in accordance with the subject's coordinates. For example, the image reconstructing unit 22 determines the generation order so that the slice images are generated in an order in the direction from the head toward the feet of the subject.

After that, the image reconstructing unit 22 generates the slice images corresponding to the regions according to the determined generation order. At that time, the image reconstructing unit 22 identifies the mode that was used when the imaging condition was set by the setting unit 26c and generates the slice images in accordance with the identified mode. For example, by referring to the mode that was input by the operator as a part of the imaging condition and stored in the storage 23, the image reconstructing unit 22 identifies the mode that was used when the imaging condition was set by the setting unit 26c.

First, an example in which the identified mode is the first mode will be explained. In the first mode, images of the imaging slices set in the detection success regions are taken by using a 2D sequence, whereas an image of the imaging region set in a range that includes the detection failure region is taken by using a 3D sequence. In that situation, the image reconstructing unit 22 first calculates an interpolation curve connecting the center coordinates of the imaging slices corresponding to the detection success regions. After that, the image reconstructing unit 22 generates the slice images corresponding to the regions in the generation order determined in advance. At that time, for example, the image reconstructing unit 22 appends identification information indicating the generation order to the slice images.

In this situation, if a slice image to be generated corresponds to a detection success region, the image reconstructing unit 22 reads a corresponding 2D image from the image storage unit 23a and determines the read 2D image to be a display-purpose slice image. In contrast, if a slice image to be generated corresponds to the detection failure region, the image reconstructing unit 22 reads a corresponding 3D image from the image storage unit 23a and generates slice images that are orthogonal to the interpolation curve calculated in advance by performing a Multi Planar Reconstruction (MPR) process, on the basis of the read 3D image. In that situation, the image reconstructing unit 22 generates the slice images at intervals that are equal to the thicknesses of the imaging slices corresponding to the detection success regions. Alternatively, the image reconstructing unit 22 may use the thicknesses of the imaging slices corresponding to the detection success regions as an initial value of the intervals and change the intervals according to an instruction from the operator.

Next, an example in which the identified mode is the second mode will be explained. In the second mode, images of an imaging region set in a range that includes both the detection success regions and the detection failure region are taken by using a 3D sequence. In that situation, the image reconstructing unit 22 first calculates an interpolation curve connecting the center coordinates of the imaging slices corresponding to the detection success regions. After that, the image reconstructing unit 22 generates the slice images corresponding to the regions in the generation order determined in advance. At that time, for example, the image reconstructing unit 22 appends identification information indicating the generation order to the slice images.

In this situation, if a slice image to be generated corresponds to a detection success region, the image reconstructing unit 22 reads a corresponding 3D image from the image storage unit 23a and generates slice images in positions corresponding to the detection success region by performing an MPR process on the basis of the read 3D image. In contrast, if a slice image to be generated corresponds to the detection failure region, the image reconstructing unit 22 reads a corresponding 3D image from the image storage unit 23a and generates slice images that are orthogonal to the interpolation curve calculated in advance, by performing an MPR process, on the basis of the read 3D image. In that situation, the image reconstructing unit 22 generates the slice images at intervals that are equal to the thicknesses of the imaging slices corresponding to the detection success regions. Alternatively, the image reconstructing unit 22 may use the thicknesses of the imaging slices corresponding to the detection success regions as an initial value of the intervals and change the intervals according to an instruction from the operator.

Next, an example in which the identified mode is the third mode will be explained. In the third mode, images of the imaging slices set in the detection success regions are taken by using a 2D sequence, whereas an image of each of the plurality of imaging slices set in a range that includes the detection failure region is taken by using a 2D sequence. In that situation, the image reconstructing unit 22 first calculates an interpolation curve connecting the center coordinates of the imaging slices corresponding to the detection success regions. After that, the image reconstructing unit 22 generates the slice images corresponding to the regions in the generation order determined in advance. At that time, for example, the image reconstructing unit 22 appends identification information indicating the generation order to the slice images.

In this situation, if a slice image to be generated corresponds to a detection success region, the image reconstructing unit 22 reads a corresponding 2D image from the image storage unit 23a and determines the read 2D image to be a display-purpose slice image. In contrast, if a slice image to be generated corresponds to the detection failure region, the image reconstructing unit 22 reads a corresponding 2D image from the image storage unit 23a and determines the read 2D image to be a display-purpose slice image. In that situation, the image reconstructing unit 22 generates slice images that are orthogonal to the interpolation curve calculated in advance, by performing an MPR process, on the basis of the plurality of 2D images corresponding to the detection failure region. Also, the image reconstructing unit 22 generates the slice images at intervals that are equal to the thicknesses of the imaging slices corresponding to the detection success regions. Alternatively, the image reconstructing unit 22 may use the thicknesses of the imaging slices corresponding to the detection success regions as an initial value of the intervals and change the intervals according to an instruction from the operator. As another example, the image reconstructing unit 22 may read 2D images at intervals that are equal to the thicknesses of the imaging slices corresponding to the detection success regions, from among the plurality of 2D images corresponding to the detection failure region and determine the read 2D images to be display-purpose slice images.

In addition, in that situation, when the display controlling unit 26e has received, via the input unit 24, an instruction from the operator indicating that the slice images of the target sites taken during a medical examination of the diagnosis target should sequentially be displayed, the display-purpose slice images generated by the image reconstructing unit 22 are sequentially read starting with the one generated first, and the display unit 25 is caused to sequentially display the read images. In that situation, for example, the display controlling unit 26e identifies the order in which the slice images were generated, on the basis of the identification information appended to the slice images.

According to the present modification example, it is possible to display the images faster than in the example in which the display-purpose slice images are generated at the point in time when an instruction is received from the operator. In another example, the display controlling unit 26e may transfer the generated display-purpose slice images to an image display device that is connected to the MRI apparatus 100 via a network. With this arrangement, by using the image display device, an image interpreting doctor, for example, who is in a location distant from the MRI apparatus 100 is able to view the slice images while switching between the slice images in the order according to the subject's coordinates.

Further, in the exemplary embodiments described above, the example in which the target sites are intervertebral discs is explained; however, the target sites may be vertebral bodies. In that situation, the first detecting unit 26a detects position information indicating positions and orientations of the vertebral bodies, with respect to the plurality of vertebral bodies, on the basis of an image rendering the spine of the subject. For example, as explained in the embodiment above, the first detecting unit 26a extracts the position information of the intervertebral discs from the image rendering the spine of the subject and determines a middle point between an i'th intervertebral disc and an (i+1)'th intervertebral disc (i: a natural number) to be the position of a vertebral body. Further, the first detecting unit 26a determines an average of the orientations of an i'th and an (i+1)'th intervertebral discs to be the orientation of a vertebral body. In this situation, the first detecting unit 26a calculates the positions and the orientations of the vertebral bodies positioned on the two ends of the spine, on the basis of change amounts in the positions and the orientations of the other vertebral bodies. After that, when the first detecting unit 26a has detected vertebral body information, the functional units included in the computer system 20 perform the same processes by replacing the intervertebral discs with the vertebral bodies.

Alternatively, it is also acceptable to use both intervertebral discs and vertebral bodies as the target sites and to take images of both in a single sequence. For example, it is acceptable to set an imaging region including a plurality of slices so as to include both the intervertebral discs and the vertebral bodies and to repeatedly perform imaging processes including both intervertebral discs and vertebral bodies in a single sequence. In yet another example, it is also acceptable to set an imaging region including a plurality of slices for intervertebral discs and for vertebral bodies, so that imaging processes including only the intervertebral discs and imaging processes including only the vertebral bodies are performed in a single sequence.

Further, the target sites are not limited to sites related to the spine. For example, the target sites may be sites related to a knee, an elbow, a shoulder, a hip joint, or the like.

For example, during a medical examination of the menisci of a knee, a plurality of slice images that are substantially orthogonal to the menisci are taken while changing the angle in a circumferential direction of the knee joint, by using a point positioned near the center of the knee joint as the center. In that situation, for example, the menisci are detected from an image of the knee joint taken along the gap between the upper-leg-side bone and the lower-leg-side bone, so that the positions of the slice images are determined on the basis of the detection result.

In that situation, for example, by using the image of the knee joint taken along the gap between the upper-leg-side bone and the lower-leg-side bone as a detection-purpose image, the detecting unit detects position information of the menisci from the detection-purpose image. Further, on the basis of the detected position information, the specifying unit determines imaging positions of the plurality of slice images that are arranged radially, by using a point positioned near the center of the knee joint as the center. After that, the acquiring unit acquires, by using a 2D sequence, data of the imaging positions determined by the specifying unit. Further, by using the data acquired by using the 2D sequence, the generating unit generates the plurality of slice images that are substantially orthogonal to the menisci.

In contrast, if the detection of any of the menisci by the detecting unit failed, the specifying specifies a detection failure region including the meniscus of which the detection failed, within the detection-purpose image. Further, in that situation, the acquiring unit acquires data of the detection failure region by using a 3D sequence. After that, by using volume data acquired by using the 3D sequence, the generating unit generates a plurality of slice images that are substantially orthogonal to the menisci, while changing the angle by predetermined degrees in a circumferential direction of the knee joint, by using a point positioned near the center of the knee joint as the center.

According to at least one aspect of the exemplary embodiments described above, even if there is a region in which the detection of the intervertebral discs or the vertebral bodies failed, it is possible to easily obtain a diagnosis image of such a region.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging (MRI) apparatus comprising:
MRI system components including processing circuitry configured to:
detect position information of each of plural target sites of a subject by analyzing previously acquired image data which was acquired using a first magnetic resonance (MR) imaging sequence;
specify, based on the image data and position information of the target sites, a first region and a second region which is different from the first region;
acquire data of the second region by using a second MR imaging condition which is different from a first MR imaging condition used for acquiring data of the first region
specify a region in which automatic detection of the target sites was successful as the first region, and
specify a region in which automatic detection of the target sites failed as the second region.

2. The magnetic resonance imaging apparatus according to claim 1, wherein the processing circuitry is further configured to generate a desired slice image including at least one target site in the second region, by performing image processing on a plurality of imaging slices acquired from the second region.

3. The magnetic resonance imaging apparatus according to claim 1, wherein the processing circuitry is configured to:
   acquire data of an imaging slice set with target sites in the first region, by using a 2D sequence, and
   acquire data of an imaging region set in a range that includes the second region, by using a 3D sequence.

4. The magnetic resonance imaging apparatus according to claim 1, wherein the processing circuitry is configured to acquire data of an imaging region set in a range that includes both the first region and the second region, by using a 3D sequence.

5. The magnetic resonance imaging apparatus according to claim 1, wherein the processing circuitry is configured to:
   acquire data of an imaging slice set with target sites in the first region, by using a first 2D sequence, and
   acquire data of each of a plurality of imaging slices set in a range that includes the second region, by using a second 2D sequence.

6. The magnetic resonance imaging apparatus according to claim 5, wherein the second 2D sequence is different from the first 2D sequence in regard to at least one of a quantity, a thickness, and a gap between imaging slices.

7. The magnetic resonance imaging apparatus according to claim 1, wherein the processing circuitry is further configured to cause display of a slice image corresponding to the first region and a slice image corresponding to the second region in an order according to subject-related coordinates.

8. The magnetic resonance imaging apparatus according to claim 1, wherein
   the image data represents an image on which a spine of the subject is visualized, and
   the target sites are at least one of (a) intervertebral discs and (b) vertebral bodies of the subject.

9. The magnetic resonance imaging apparatus according to claim 1, wherein the processing circuitry is configured to, with respect to the target sites detected from the image data, the specifying unit calculates calculate a distance between target sites for each of sets of adjacent target sites and, when there is at least one set of which the calculated distance is longer than a reference value, the specifying unit specifies specify a range positioned between the target sites in the set as the second region.

10. A magnetic resonance imaging apparatus comprising:
   MRI system components including processing circuitry configured to:
   detect position information of each of plural target sites of a subject by analyzing previously acquired image data which was acquired using a first magnetic resonance (MR) imaging sequence;
   detect, based on positional relationships of the detected target sites, a region for which position information has not been successfully detected, and specify that as a detection failure region; and
   acquire data of the detection failure region by using a 3D MR imaging sequence.

\* \* \* \* \*